US012613241B2

(12) United States Patent
Sakai et al.

(10) Patent No.:     US 12,613,241 B2
(45) Date of Patent:        Apr. 28, 2026

(54) IMMUNOCHROMATOGRAPHIC TEST STRIP

(71) Applicant: SEKISUI MEDICAL CO., LTD., Tokyo (JP)

(72) Inventors: Shun Sakai, Tokyo (JP); Keigo Kohno, Tokyo (JP); Kanako Itou, Tokyo (JP); Akira Nakajima, Tokyo (JP); Motoki Morita, Tokyo (JP)

(73) Assignee: SEKISUI MEDICAL CO., LTD., Tokyo (JP)

( * ) Notice: Subject to any disclaimer, the term of this patent is extended or adjusted under 35 U.S.C. 154(b) by 686 days.

(21) Appl. No.: 17/277,880

(22) PCT Filed: Sep. 26, 2019

(86) PCT No.: PCT/JP2019/037748
§ 371 (c)(1),
(2) Date: Mar. 19, 2021

(87) PCT Pub. No.: WO2020/067233
PCT Pub. Date: Apr. 2, 2020

(65) Prior Publication Data
US 2021/0349085 A1      Nov. 11, 2021

(30) Foreign Application Priority Data

Sep. 27, 2018    (JP) ................................ 2018-181825
Feb. 5, 2019     (JP) ................................ 2019-018924

(51) Int. Cl.
*G01N 33/543*        (2006.01)
*G01N 21/77*         (2006.01)
*G01N 21/84*         (2006.01)

(52) U.S. Cl.
CPC ... *G01N 33/54387* (2021.08); *G01N 21/8483* (2013.01); *G01N 33/54306* (2013.01); *G01N 2021/7759* (2013.01)

(58) Field of Classification Search
CPC ......... G01N 33/54387; G01N 21/8483; G01N 33/54306; G01N 2021/7759;
(Continued)

(56) References Cited

U.S. PATENT DOCUMENTS 4,780,280 A * 10/1988 Berger ................. G01N 33/525
                                                              422/401
4,855,228 A *  8/1989 Charlton ................. C12Q 1/28
                                                              435/14
(Continued)

FOREIGN PATENT DOCUMENTS

CN        204241478 U    4/2015
EP        2 273 269 A1   1/2011
(Continued)

OTHER PUBLICATIONS

Wong, R. et al., Lateral Flow Immunoassay, Humana Press. p. 1-5, 51-53, 97-98. (2009). (Year: 2009).*
(Continued)

*Primary Examiner* — Christopher L Chin
*Assistant Examiner* — Ellis Follett Lusi
(74) *Attorney, Agent, or Firm* — Birch, Stewart, Kolasch & Birch, LLP

(57)                    ABSTRACT
A problem to be solved is to provide a test strip capable of avoiding occurrence of a so-called bleaching phenomenon in an immunochromatographic test strip to enable better detection and visibility. Another problem to be solved is to provide an immunochromatographic test strip capable of preventing a variation in detection value on a test line.
The problems are solved by an immunochromatographic test strip including at least a porous membrane and having a
(Continued)

sample application region, a development region, and a detection region in which a specific binding substance is immobilized, wherein the detection region is immobilized on a front surface of the porous membrane, and wherein an opaque base material having a thickness of 30 μm or more and 200 μm or less is placed on the back surface of the porous membrane.

25 Claims, 4 Drawing Sheets

(58) Field of Classification Search
CPC ....... G01N 33/54388; G01N 33/54366; G01N 33/532; G01N 33/558; G01N 33/54389; B01L 2300/0825
USPC ....... 422/400, 401, 420, 421, 425, 426, 430; 435/287.7, 287.9, 970, 805, 810; 436/169, 170, 514, 518, 530, 810
See application file for complete search history.

(56) References Cited

U.S. PATENT DOCUMENTS

| | | | | |
|---|---|---|---|---|
| 5,411,858 | A * | 5/1995 | McGeehan | B01L 3/5023 436/805 |
| 6,194,221 | B1 * | 2/2001 | Rehg | G01N 33/54388 436/514 |
| 6,497,842 | B1 | 12/2002 | Takahashi et al. | |
| 7,239,394 | B2 * | 7/2007 | Sharrock | G01N 21/274 356/436 |
| 7,790,439 | B2 * | 9/2010 | Nadaoka | G01N 33/54388 436/514 |
| 8,105,843 | B2 * | 1/2012 | Buchanan | B01L 3/5023 436/805 |
| 9,110,058 | B2 | 8/2015 | Yoshimizu et al. | |
| 9,599,609 | B2 * | 3/2017 | Mehra | G01N 33/54393 |
| 9,702,872 | B1 * | 7/2017 | Wang | B01L 3/502761 |
| 2005/0277202 | A1 * | 12/2005 | Fleming | G01N 33/54388 436/514 |
| 2007/0287198 | A1 * | 12/2007 | LaBorde | G01N 33/54326 436/524 |
| 2011/0045578 | A1 * | 2/2011 | Kawamata | G01N 33/558 435/287.1 |
| 2012/0252004 | A1 | 10/2012 | Wada et al. | |
| 2014/0087365 | A1 * | 3/2014 | Morita | G01N 33/54388 435/7.1 |
| 2014/0121125 | A1 * | 5/2014 | Mehra | G01N 33/6854 506/18 |
| 2015/0010918 | A1 | 1/2015 | Ruvinsky | |
| 2016/0209410 | A1 | 7/2016 | Fukushima et al. | |
| 2016/0377616 | A1 | 12/2016 | Nishitani | |
| 2018/0284115 | A1 * | 10/2018 | Suzuki | G01N 33/54393 |
| 2019/0094215 | A1 | 3/2019 | Itou et al. | |
| 2019/0145970 | A1 | 5/2019 | Nishitani et al. | |

FOREIGN PATENT DOCUMENTS

| | | |
|---|---|---|
| EP | 2 506 013 A2 | 10/2012 |
| EP | 2 506 013 A3 | 2/2013 |
| EP | 3 076 177 A1 | 10/2016 |
| JP | 2017-186262 A | 10/2017 |
| JP | 6464308 B1 | 2/2019 |
| JP | 2020-125994 A | 8/2020 |
| KR | 1 104 886 A1 | 6/2001 |
| KR | 10-2001-0072828 A | 7/2001 |
| WO | WO 2009/136476 A1 | 11/2009 |
| WO | WO 2010/001598 A1 | 1/2010 |
| WO | WO 2013/108250 A1 | 7/2013 |
| WO | WO 2015/012384 A1 | 1/2015 |
| WO | WO 2015/080286 A1 | 6/2015 |
| WO | WO 2017/170824 A1 | 10/2017 |
| WO | WO 2018/012517 A1 | 1/2018 |

OTHER PUBLICATIONS

Bangs Laboratories, "TechNote 301, Immunological application, Beads Above the Rest," Immunological Application 9025 Technology Dr. Fishers, IN 46038-2886, Mar. 20, 2013, [online], URL: https://www.bangslabs.com/sites/default/files/imce/docs/TechNote%20301%20Web.pdf, pp. 1-13.
Extended European Search Report for European Application No. 19864035.1, dated May 30, 2022.
International Search Report, issued in PCT/JP2019/037748, dated Feb. 4, 2020.
Japanese Notice of Reasons for Refusal, issued in Application No. 2018-181825, dated Oct. 24, 2018.
Written Opinion of the International Searching Authority, issued in PCT/JP2019/037748, dated Feb. 4, 2020.
English translation of International Preliminary Report on Patentability and Written Opinion mailed Apr. 8, 2021, in PCT/JP2019/037748.
Chinese Office Action and Search Report for corresponding Chinese Application No. 201980061831.0, dated Feb. 23, 2024, with English translation.
European Communication pursuant to Article 94(3) EPC for corresponding European Application No. 19864035.1, dated Jan. 31, 2024.
Korean Office Action for Korean Application No. 10-2021-7011183, dated Apr. 28, 2024, with English translation.
Chinese Office Action for Chinese Application No. 201980061831.0, dated Sep. 30, 2024, with an English translation.
Chinese Office Action for Chinese Application No. 201980061831.0, dated May 28, 2024, with English translation.
Chinese Office Action for Chinese Application No. 201980061831.0, dated Jul. 25, 2024, with an English translation.

* cited by examiner (A)

(B)

IMMUNOCHROMATOGRAPHIC TEST STRIP

TECHNICAL FIELD

The present invention relates to an immunochromatographic test strip and an immunochromatographic detection method using the test strip.

BACKGROUND ART

As POCT (point of care testing) for treatment near patients becomes widespread, a lateral flow immunochromatographic detection method using a test strip made up of a nitrocellulose membrane etc. has become widely used as a simple immunoassay utilizing antigen-antibody reactions.

An immunochromatography based test strip (herein referred to as an immunochromatographic test strip) generally consists of a sample application region, a development region and a detection region located on a porous membrane. The membrane is structured so that a detection antibody targeting a specific analyte binds with the sample and is able to travel down the development region to the detection region. The antibodies responsible for analyte detection become fixed in a certain spot on the development region known as the detection region.

When the specimen is dropped onto the sample application region, and the specimen contains an analyte, the analyte specifically binds to the labeled antibody to form a complex. The complex is developed in the development region downstream direction and binds to the immobilized antibody for detection in the detection region. Therefore, the analyte can qualitatively or quantitatively be analyzed by detecting a sandwich complex of the labeled antibody, the analyte, and the immobilized antibody in the detection region.

Methods of detecting a complex between an analyte and a conjugate in the detection region of the immunochromatography test strip having the configuration described above include a method of measuring an intensity of reflected light from a label to calculate an absorbance (reflection absorbance). The reflection absorbance is calculated by using a ratio of the reflected light intensity measured at the detection line of an analyte and two neighboring regions either side of the detection region If this method is used, a measurement waveform may be disturbed due to a non-specific increase near the upstream side or the downstream side of the detection region where the complex is detected. In this case, when the concentration of the analyte is low, the disturbance of the measurement waveform cannot be ignored and the baseline cannot be subtracted, a specific signal (peak) cannot accurately be detected, which may make the measurement itself impossible.

Since the frequency of disturbances in the measurement waveform and the level of disturbance of the measurement waveform are not constant, the reproducibility of each measurement is reduced and a correction to a suitable measurement value (in other words, confirmation of the measurement waveform) must be made in each measurement.

In a regular immunochromatographic detection method using a white membrane, the disturbance of the measurement waveform can visually be observed as a phenomenon in which a specific site on the membrane looks relatively whiter than the surrounding color as if the site is bleached (a so-called bleaching phenomenon; hereinafter also simply referred to as bleaching). This hinders visual confirmation of the colors produced by the label and can lead to diminishing test result accuracy.

Although the cause of such bleaching is not known, it is supposedly caused by differences in manufacturing lots of test strips, differences in storage conditions of test strips, and differences in manufacturing conditions such as pretreatment conditions of test strips.

Regarding a method for eliminating such a bleaching phenomenon, the following documents are known.

Patent Document 1 discloses an assay using a sample diluent to which methanol is added for preventing the bleaching often observed when an immunochromatographic test strip is stored over a long term.

Patent Document 2 discloses a method of preventing the bleaching and the disturbance of the measured waveform by treating an antibody-immobilized membrane of an immunochromatographic test strip with a specific surfactant such as n-octyl-$\beta$-D-glucoside.

CITATION LIST

Patent Literature

Patent Document 1: WO 2015/080286
Patent Document 2: WO 2010/001598

SUMMARY OF INVENTION

Technical Problem

A problem to be solved by the present invention is to provide a test strip capable of avoiding the occurrence of a so-called bleaching phenomenon in an immunochromatographic test strip and enabling detection with better visibility by an approach completely different from the prior art. Another problem to be solved by the present invention is to provide an immunochromatographic test strip capable of preventing a variation in detection value on a test line.

Solution to Problem

The present inventors attempted to change various elements of an immunochromatographic test strip so as to solve the problems and surprisingly found that bleaching near a test line can be avoided and a variation in detection value can be prevented by placing an opaque base material on a back surface of a porous membrane on which a specific binding substance such as an antibody is immobilized on the front surface in the immunochromatographic test strip including the porous membrane, thereby completing the present invention. Specifically, the present invention has the following configurations.

(1) An immunochromatographic test strip comprising at least a porous membrane, the immunochromatographic test strip including a sample application region, a development region, and a detection region, wherein the detection region is immobilized on a front surface of the porous membrane, and wherein an opaque base material is placed on a back surface of the porous membrane.

(2) The immunochromatographic test strip according to (1), wherein the opaque base material is a white base material.

(3) The immunochromatographic test strip according to (1) or (2), wherein the thickness of the opaque base material is 30 $\mu$m or more and 200 $\mu$m or less.

(4) The immunochromatographic test strip according to any one of (1) to (3), wherein the opaque base material is placed for a lining of the porous membrane, and wherein a backing sheet is placed under the opaque base material.

(5) The immunochromatographic test strip according to any one of (1) to (4), further comprising a sample pad serving as the sample application region, and a conjugate pad containing a specific binding substance labeled with colloidal gold or colored latex.

(6) The immunochromatographic test strip according to any one of (1) to (5), wherein the specific binding substance is an antibody.

(7) The immunochromatographic test strip according to any one of (1) to (6), wherein the immunochromatographic test strip is a test strip for detection by optical means.

(8) An immunochromatographic detection kit comprising: the immunochromatographic test strip according to any one of claims (1) to (7).

(9) An immunochromatographic detection method comprising: using a following test strip:

an immunochromatographic test strip comprising a porous membrane that includes at least a detection region with an opaque base material placed on the back surface of the porous membrane.

(10) The immunochromatographic detection method according to (9), wherein the opaque base material is a white base material.

(11) The immunochromatographic detection method according to (9) or (10), wherein the thickness of the opaque base material is 30 μm or more and 200 μm or less.

(12) The immunochromatographic detection method according to any one of (9) to (11), wherein the opaque base material is placed for a lining of the porous membrane, and wherein a backing sheet is placed under the opaque base material.

(13) The immunochromatographic detection method according to any one of (9) to (12), wherein the test strip further comprises a sample pad serving as the sample application region, and a conjugate pad containing a specific binding substance labeled with colloidal gold or colored latex.

(14) The immunochromatographic detection method according to any one of (9) to (13), wherein the specific binding substance is an antibody.

(15) The immunochromatographic detection method according to any one of (9) to (14), comprising a step of detecting an optical parameter derived from a labeling substance by optical means.

(16) The immunochromatographic detection method according to any one of (9) to (15), comprising a step of determining a coloration derived from a labeling substance by visual observation.

(17) A method for reducing variation in measurement values in an immunochromatographic detection method, the method comprising: using a following test strip:

an immunochromatographic test strip comprising at least a porous membrane wherein the immunochromatographic test strip includes a sample application region, a development region, and a detection region, wherein the detection region is immobilized on the front surface of the porous membrane, and wherein an opaque base material is placed on the back surface of the porous membrane.

(18) The method for reducing the variation according to (17), wherein the opaque base material is a white base material.

(19) The method for reducing the variation according to (17) or (18), wherein the thickness of the opaque base material is 30 μm or more and 200 μm or less.

(20) The method for reducing the variation according to any one of (17) to (19), wherein the opaque base material is a member placed for a lining of the porous membrane, and wherein a backing sheet is placed under the opaque base material.

(21) A method for reducing bleaching of a test strip in an immunochromatographic detection method using a test strip, the method comprising: using following test strip:

an immunochromatographic test strip comprising at least a porous membrane wherein the immunochromatographic test strip includes a sample application region, a development region, and a detection region, wherein the detection region is immobilized on a front surface of the porous membrane, and wherein an opaque base material is placed on a back surface of the porous membrane.

(22) The method for reducing bleaching of a test strip according to (21), wherein the opaque base material is a white base material.

(23) The method for reducing bleaching of a test strip according to (21) or (22), wherein the thickness of the opaque base material is 30 μm or more and 200 μm or less.

(24) The method for reducing bleaching of a test strip according to any one of (21) to (23), wherein the opaque base material is placed for a lining of the porous membrane, and wherein a backing sheet is placed under the opaque base material.

Advantageous Effects of Invention

The present invention can provide an immunochromatographic test strip capable of avoiding bleaching near the test line and therefore excellent in visibility at the time of visual detection and causing less variations in values measured by optical means.

DESCRIPTION OF EMBODIMENTS (Immunochromatographic Test Strip)

Figure 1:
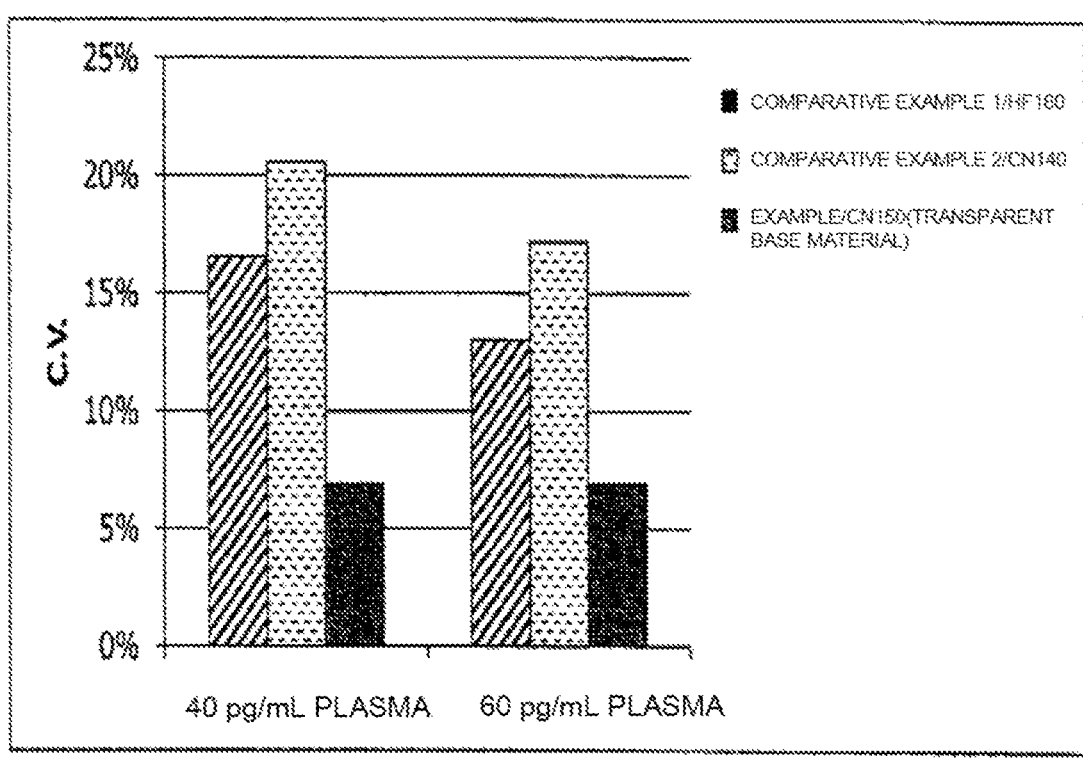
FIG. 1 is a graph showing variations in measurement values when immunochromatographic measurement is performed with an immunochromatographic test strip using a porous membrane in which a lining is made of a transparent base material (Comparative Example) or a white base material (present invention). (Test Example 2, an analyte is on the medium concentration side)

An immunochromatographic test strip of the present invention includes "a sample application region", "a development region" and "a detection region" within a porous membrane. A labeled specific binding substance binding to an analyte is held in a manner which allows the sample to be eluted and then flow through the development region and arrives at the detection site. Furthermore the specific binding substance used for detection becomes fixed to a specific portion of the development region which constitutes the detection region.

An example of a test strip embodying these elements is a test strip including a sample pad serving as the sample application region, a conjugate pad holding a labeled specific binding substance binding to an analyte which can be eluted, and a porous membrane which can fix the specific binding substance to a specific site on the membrane and serve as the development region and the detection region. Specifically, a typical test strip for immunochromatography of the present invention has the following configuration:

(1) a sample pad to which a specimen is loaded;

(2) a conjugate pad placed downstream of the sample pad and holding a conjugate sensitized with a first specific binding substance on a colloidal gold surface in an elutable manner;

(3) a porous membrane placed downstream of the conjugate pad and having on the front surface a detection region in which a second specific binding substance binds to a complex formed by the conjugate and an analyte causing the analyte to be immobilized, with an opaque base material placed on the back surface.

The sample pad, the conjugate pad, and the porous membrane may each constitute a separate carrier, or two of them may constitute one carrier, and any form may be available as long as the sample pad, the conjugate pad, and the porous membrane are placed in this order from upstream to downstream.

In addition to the constituent elements described above, the immunochromatographic test strip may have one or more of absorption pads and 3rd pads further placed and mounted thereon.

The test strip is usually arranged on a solid phase support such as a plastic adhesive sheet (hereinafter also referred to as a backing sheet).

A polyester film etc., may be laminated on the test strip for the purpose of increasing the mechanical strength of the porous membrane on which the specific binding substance is immobilized and preventing evaporation of moisture (drying) during an assay.

A detection method using the immunochromatographic test strip of the present invention is performed as follows.

When the specimen is dropped onto the sample application region and the specimen contains an analyte, the analyte specifically binds to the labeled specific binding substance to form a complex. The complex is developed in the development region in the downstream direction and binds to the specific binding substance immobilized in the detection region. In the detection region, a sandwich type complex of the labeled specific binding substance, the analyte, and the immobilized specific binding substance is formed, and therefore, the analyte can qualitatively or quantitatively be analyzed by detecting this complex. Examples of the detection include a method of determining coloration by visual observation and a method of detecting an optical parameter derived from a label by an optical means. When the optical means is used, detection can manually or automatically be performed, and continuous measurement can also be performed.

(Sample Pad)

The sample pad used in the present invention is a site serving as the sample application region receiving a sample, and any substances and forms are available as long as those in a state of being molded into a pad can absorb a liquid sample and allow passage of the liquid and the components of the analyte.

The sample pad of the present invention can be pretreated to improve permeability.

When whole blood is measured, an erythrocyte agglutinating agent can be added. In this case, the agent may be contained in at least a portion of the sample pad or may be contained in the whole thereof.

Specific examples of materials suitable for the sample pad include, but not limited to, glass fiber, acrylic fiber, hydrophilic polyethylene material, dry paper, paper pulp, woven fabric, etc. Preferably, a glass fiber pad is used. The sample pad can also have a function of a conjugate pad described later. The sample pad, without deviation from the inventions desired function, can also contain a blocking reagent as needed in a manner which does not affect the reaction of the detection mechanism.

(Conjugate)

In the conjugate of the present invention, a specific binding substance or a control substance binding to an analyte is immobilized on a label.

The label used in the present invention may be any label capable of constituting the conjugate through conjugation (immobilization) of the specific binding substance such as an antibody and capable of serving as the label in a method in which the label is brought into contact with a sample to detect an object (such as antigen) in the sample, and examples thereof include colloidal gold particles, colloidal platinum particles, colored latex particles, and magnetic particles, among which colloidal gold and colored latex are desirable, and colloidal gold is more desirable. The particle diameter thereof may be adjusted such that a desired detection sensitivity of a measurement object is obtained depending on each type and, for example, the particle diameter of the colloidal gold particles is preferably 20 to 100 nm, more preferably 30 to 100 nm, most preferably 60 nm.

In the conjugate of the present invention, a region on the colloidal gold particle not bound to the specific binding substance can be blocked with a blocking agent.

Regarding the form of the conjugate, the conjugate may be present in a form present as the conjugate pad, i.e., in a state of being contained in a dedicated pad (conjugate pad) other than the sample pad, the third pad, and the porous membrane (type A), or may be present as a conjugate part in a portion of the sample pad (type B). Alternatively, the conjugate may be present as a separate conjugate reagent separately from the test strip so as to be mixed with the specimen (type C).

The test strip having the conjugate in the presence form of the type A will hereinafter be described.

Figure 4:
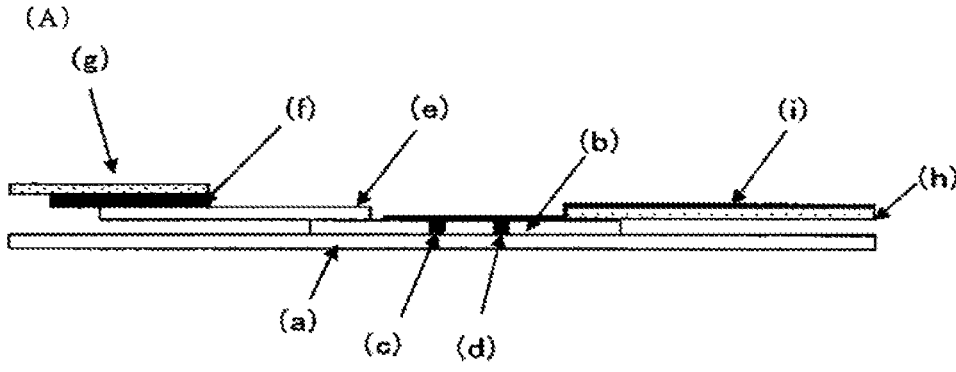
FIG. 4 is a perspective view showing an immunochromatographic test strip of the present invention. A shows the entire immunochromatographic test strip, and B shows a porous membrane.
Figure 4:
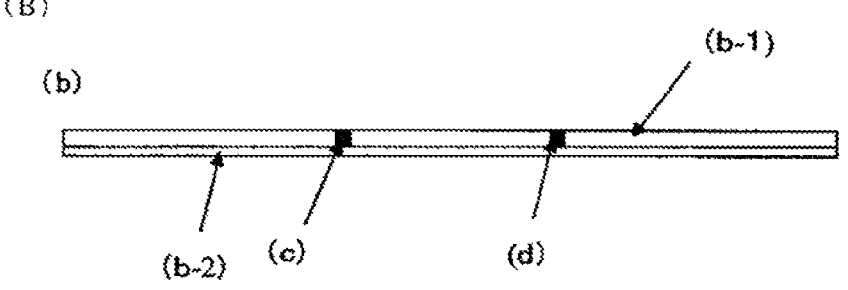

The sample pad, the conjugate pad, the third pad, and the porous membrane are arranged in this order from upstream to downstream in the flow direction of the sample and are arranged such that upper and lower layers at least partially overlap with each other. A test strip of such an arrangement example is shown in FIG. 4.

When a sample containing an analyte is loaded to the sample pad of such a test strip, the analyte flows through the sample pad to the conjugate pad on the downstream side. In the conjugate pad, the analyte and the conjugate come into contact with each other and pass through the pad while forming a complex. Subsequently, the complex passes through the third pad placed in contact with the lower surface of the conjugate pad and is developed into the porous membrane.

Since the porous membrane has the specific binding substance binding to an analyte immobilized on a portion thereof, the complex is bound and immobilized onto this membrane. The immobilized complex is detected by a means detecting absorbance, reflected light, fluorescence, magnetism, etc. derived from a labeling substance.

The test strip having the conjugate in the presence form of the type B will then be described.

A difference from the type A test strip is that the sample pad and the conjugate pad are integrated, i.e., that the sample application region and the conjugate part are formed in portions of the sample pad.

The sample application region is a site to which the sample containing an analyte is loaded, while the conjugate part is a site containing the conjugate, and the sample application region is located upstream of the conjugate part.

The test strip having the conjugate in the presence form of the type C will then be described.

The difference from the type A test strip is that the conjugate pad is absent in the test strip and that the conjugate is present as a separate conjugate reagent. For example, a filter chip may be included that has the conjugate incorporated in a filter. By using such a filter chip to filter a specimen with the filter, the conjugate held in the filter and the analyte are combined to form a complex (aggregate). This complex can be loaded to the same test strip as the type A with the absence of the conjugate pad, so as to detect the analyte.

(Detection Reagent)

In the present invention, the "detection reagent" is specifically a solution containing at least a conjugate.

The detection reagent may contain, for example, one or more types of stabilizers, solubilizers, etc. for the purpose of maintaining the conjugate in a stable state so as to facilitate the specific reaction of the specific binding substance such as an antibody immobilized on the conjugate with the analyte when mixed with the sample, or to rapidly and effectively dissolve and fluidize the conjugate. Examples of the stabilizers, solubilizers, etc. include bovine serum albumin (BSA), sucrose, casein, and amino acids.

The detection reagent may also contain known sensitizers and chelating agents such as EDTA and EGTA as needed for the purpose of improving the detection sensitivity.

In this description, the term "detection" or "measurement" must be construed in the broadest sense, including the existence proof and/or the quantitation of the analyte and must not be construed in a limited manner in any sense.

(Sample Diluent)

With this invention, when the concentration of the analyte within the sample requires dilution a diluent may be used. The diluent may be employed in instances such as when there is inhibition between the analyte and the specific binding substance or the reaction becomes accelerated resulting in aggregation of the detection label and impaired capillary flow, as long as the analyte concentration remains at a level where it can react with the specific binding substance and produce a positive signal.

(Conjugate Pad)

In the present invention, the "conjugate pad" refers to a pad acquired by drying a material suitable for the conjugate pad described later imbued with a detection reagent specifically reactive with the analyte. The conjugate pad has a function of allowing the detection reagent and the analyte to form a complex when the sample passes through the conjugate pad. The conjugate pad itself may be placed in contact with the porous membrane on which the specific binding substance is immobilized. Alternatively, the conjugate pad may be placed in contact with the sample pad so as to receive a specimen passing through the sample pad via capillary flow and then transfer the specimen via capillary flow to the 3rd pad in contact with a surface different from the contact surface of the sample pad.

Examples of materials suitable for the conjugate pad include, but not limited to, paper, cellulose mixture, nitrocellulose, polyester, acrylonitrile copolymer, glass fiber, and nonwoven fiber such as rayon. Preferably, a glass fiber pad is used.

The conjugate pad may contain a "control reagent" for ensuring reliability of an immunochromatographic detection method, for example, an antibody labeled with a label and not reactive with a specimen component, and a highly antigenic protein such as KLH (keyhole limpet hemocyanin) labeled with a label, as needed. These control reagents are components (substances) as having no possibility of presence in the sample and can appropriately be selected.

(3rd Pad)

In the present invention, the 3rd pad can be added for the purpose of removing reactive components unnecessary for detection of the analyte in the specimen and the detection reagent so that components necessary for reaction can successfully be developed in the porous membrane on which the specific binding substance is immobilized. For example, blood cells and insoluble blood cell fractions are desirably removed as the components unnecessary for detection. The 3rd pad may also have an additional effect of preliminarily removing aggregates generated through the reaction between the analyte and specific binding substance that have grown to a size preventing the movement to and the smooth development through the membrane on which the specific binding substance is immobilized.

The 3rd pad may be made of any material and in any form allowing the passage of liquid and a component to be detected as well as the detection reagent. Specific examples include, but not limited to, glass fiber, acrylic fiber, hydrophilic polyethylene material, dry paper, paper pulp, fabric, etc. The 3rd Pad may be referred to as a blood cell separation membrane when used for the purpose of separating blood cells. In the present invention, where whole blood is used as a specimen, the blood cell separation membrane is desirably used when separation and removal of the blood cells cannot be completed by the sample pad alone.

(Erythrocyte Agglutinating Agent)

In the present invention, when whole blood is used as a specimen, an erythrocyte agglutinating agent or an erythrocyte binding component is desirably used together in addition to the use of the 3rd Pad. Although the erythrocyte agglutinating agent or the erythrocyte binding component to be used together is not particularly limited, known examples thereof include lectin, a polyclonal antibody, and a monoclonal antibody, and a polycationic erythrocyte agglutinating agent is also usable. Examples of known polycationic erythrocyte agglutinating agents include polybrene, polylysine, polyacrylic amine, and polyalanine, and polybrene is preferable among them. Polybrene has a chemical name, hexadimethrine bromide, and is one of cationic polymers to which CAS No. 28728-55-4 is assigned.

The erythrocyte agglutinating agent or the erythrocyte binding component can be used in a form in which the agent or the component is added to a diluent for diluting a specimen or directly added to a specimen, or can be contained in the sample application region (sample pad) of the immunochromatographic test strip. In such a use form, erythrocytes in whole blood are agglutinated.

(Porous Membrane)

The porous membrane used in the immunochromatographic test strip of the present invention is characterized in that the specific binding substance for detection is immobilized on the front surface thereof while an opaque base material is placed on the back surface.

The opaque base material of the present invention placed on the back surface of the porous membrane is a placed to line the membrane since the membrane is porous, and is an impermeable film. Such an opaque base material of the present invention may also be referred to as a so-called "lining material". The base material can be affixed to the back surface of the porous membrane for lining, or the porous membrane can be laminated on the upper surface of an impermeable film in advance.

The opaque base material of the present invention may be placed on the back surface of the porous membrane and may be in contact with the membrane via an adhesive layer or may be in contact with the membrane without the adhesive layer if adhesiveness is ensured. When a backing sheet described later is placed, the backing sheet is placed under the opaque base material (lining material) of the present invention.

In the present invention, the opaque base material is used as the conventionally transparent base material on the back surface of the porous membrane, so as to avoid a so-called "bleaching phenomenon" (hereinafter also simply referred to as bleaching) in which a corresponding site on the membrane looks relatively whiter than the surrounding color as if the site is bleached.

The thickness of the opaque base material of the present invention (not including the adhesive layer etc.) may be set such that the base material can function as the lining material of the porous membrane and is preferably 30 μm or more and 200 μm or less, more preferably 60 μm or more and 140 μm or less, most preferably 80 μm or more and 120 μm or less.

Being opaque means not being transparent or that the other side cannot be seen through, and although complete opacity is not required, complete opacity is more preferable.

The opaque base material is preferably a base material having a color similar to that of the porous membrane, and when the porous membrane is white, the base material of the present invention is desirably cream or gray close to white, and white is most preferable.

The opaque base material may be any water-impermeable opaque base material and may be made of any material. Examples of the material include polyethylene, polyethylene terephthalate, polyester, nylons, etc.

By placing the opaque base material of the present invention on the back surface of the porous membrane, a variation in measurement value on a test line can be suppressed. Although the reason is not known, it is presumed that the matching of coloring on the top and back surfaces of the membrane leads to a reduction in the non-uniform appearance of a surface component (nitrocellulose), or a reduction in interference caused by reflected light of the backing sheet placed under the lower layer of the membrane, etc., thereby resulting in an improvement in reproducibility.

The porous membrane (hereinafter also simply referred to as a membrane) can be made of any material. Examples thereof include, but not limited to, porous membranes of polyethylene, polyethylene terephthalate, nylons, glass, polysaccharides such as cellulose and cellulose derivatives, or ceramics. Specific examples can include glass fiber filter paper and nitrocellulose membrane commercially available from Merck Millipore, Toyo Roshi Kaisha, GE Healthcare, etc. By appropriately selecting a pore size and a structure of the porous membrane, the rate of the immune complex consisting of the labeled specific binding substance and the analyte flowing through the membrane can be controlled. Since an amount of the labeled specific binding substance binding to the specific binding substance immobilized on the membrane can be adjusted by controlling the flow rate in the membrane, the pore size and the structure of the membrane are desirably optimized in consideration of combination with other constituent materials of the immunochromatographic test strip of the present invention.

(Immobilization of Specific Binding Substance on Porous Membrane)

The specific binding substance such as an antibody to the analyte of the present invention can be immobilized on the porous membrane by a generally well-known method. For example, in the case of the flow-through type, the specific binding substance is adjusted to a predetermined concentration, and a constant amount of the solution thereof is applied to the porous membrane in a specific symbol shape such as a dot or +. In this case, to ensure the reliability of the immunochromatographic detection method, a protein or compound capable of binding to the conjugate is typically immobilized at a position different from the specific binding substance binding to the analyte to form a "control line". The specific binding substance binding to the control reagent described above can be immobilized at a position different from the specific binding substance binding to the analyte to form a "control line".

In the case of the lateral-flow type, the specific binding substance is adjusted to a predetermined concentration, and the solution thereof is applied in a line shape to the porous membrane using an apparatus etc. which has a mechanism capable of moving a nozzle in a horizontal direction while discharging the solution at a constant rate therefrom. In this case, the concentration of the specific binding substance is preferably 0.1 to 5 mg/mL, more preferably 0.5 to 3 mg/mL. An amount of the specific binding substance immobilized on the porous membrane can be optimized by adjusting an amount of application dropped onto the porous membrane in the case of the flow-through type, and can be optimized by adjusting a rate of discharge from the nozzle of the apparatus described above in the case of the lateral-flow type. Particularly, in the case of the lateral-flow type, 0.5 to 2 μL/cm is preferable.

In the present invention, the term "flow through membrane assay" refers to a method in which a specimen solution etc. are developed to pass perpendicularly through the porous membrane, and the term "lateral flow membrane assay" refers to a method in which a specimen solution etc. are developed to move in a direction parallel to the porous membrane.

In the present invention, regarding the position of application of the specific binding substance binding to the object onto the porous membrane, in the case of the lateral-flow type, the position can be arranged such that the detection reagent developed from the conjugate pad due to the capillarity sequentially passes through lines to which respective specific binding substances are applied. Preferably, the line formed by applying the specific binding substance binding to the analyte is located upstream, and the line formed by applying the control specific binding substance is preferably located downstream thereof. In this case, the lines are desirably spaced at a sufficient distance so that the signal of the label can be detected. Even in the case of the flow-through type, the position of application of the specific binding substance binding to the object may be arranged so that the signal of the label can be detected.

The specific binding substance solution applied to the porous membrane can usually be prepared by using a predetermined buffer solution. Examples of the type of the buffer solution include commonly used buffer solutions such as phosphate buffer solution, Tris buffer solution, and Good's buffer solution. The pH of the buffer solution is preferably in a range of 6.0 to 9.5 and may appropriately be adjusted depending on a property of the specific binding substance to be used.

For example, a buffer solution having a pH of 8.0 can be used for an anti-cTnI antibody described later. The buffer solution may further contain salts such as NaCl, stabilizers and preservatives such as sucrose, preservatives such as ProClin, etc. The salts include those contained for adjusting the ionic strength such as NaCl, and those added at the step of adjusting the pH of the buffer solution such as sodium hydroxide. After immobilizing the specific binding substance on the porous membrane, blocking can further be performed by coating an area other than the specific binding substance immobilization site with a normally used blocking agent turned into the form of solution or vapor. In this description, the porous membrane having the specific binding substance immobilized thereon as described above may be referred to as a "specific binding substance-immobilized membrane".

(Absorption Pad)

In the present invention, the absorption pad is a site having liquid absorbability for controlling the development of the specimen by absorbing the specimen having moved and passed through the porous membrane. In the lateral-flow type, the absorption pad may be placed on the most downstream side of the test strip, and in the flow-through type, the absorption pad may be placed on a lower portion of the specific binding substance-immobilized membrane, for example. For the absorption pad, for example, filter paper can be used; however, the present invention is not limited thereto.

(Backing Sheet)

In the present invention, the backing sheet is a solid phase for supporting the test strip, and a plastic sheet with an adhesive material attached thereto is usually used. Examples of the material of the backing sheet include, but are not limited to, polystyrene, polyester, polypropylene, vinyl chloride, etc. Although the color of the backing sheet is not particularly limited, the color is preferably the same color as the membrane, and when the membrane is white, the backing sheet is also preferably white.

The thickness (not including the adhesive layer etc.) of the backing sheet of the present invention may be adjusted such that the backing sheet can function as a supporting member of the test strip and is preferably 10 μm or more and 600 μm or less, more preferably 150 μm or more and 350 μm or less, and most preferably 200 μm or more and 320 μm or less.

(Top Film)

In the present invention, a top film refers to a sheet-shaped member covering the uppermost surface of the test strip and is used for the purpose of increasing the mechanical strength of a porous membrane on which a specific binding substance is immobilized and preventing evaporation of moisture (drying) during an assay. The material of the top film may be any material capable of achieving the object, such as polyester, and can coat the test strip by using an adhesive material or can be laminated. In the present invention, it was found that the bleaching phenomenon strengthened by coating the test strip with the top film can be weakened by making the backing member of the membrane opaque. Therefore, the effect of the present invention becomes more remarkable in the test strip provided with the top film.

The thickness (not including the adhesive layer etc.) of the top film of the present invention may be adjusted such that the function of protecting the membrane and preventing evaporation of moisture during an assay is implemented, and is preferably 10 μm or more and 150 μm or less, more preferably 20 μm or more and 80 μm or less.

(Detection Device)

Figure 5:
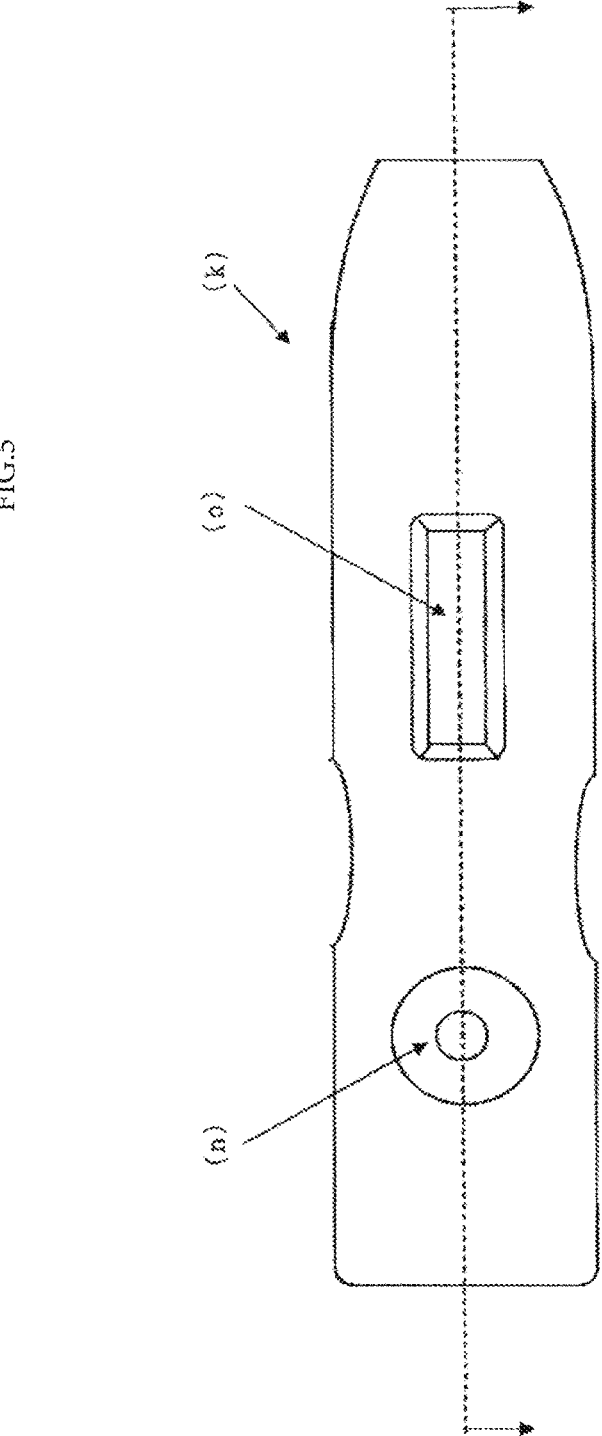
FIG. 5 is a top view of an immunochromatographic detection device of the present invention.
Figure 6:
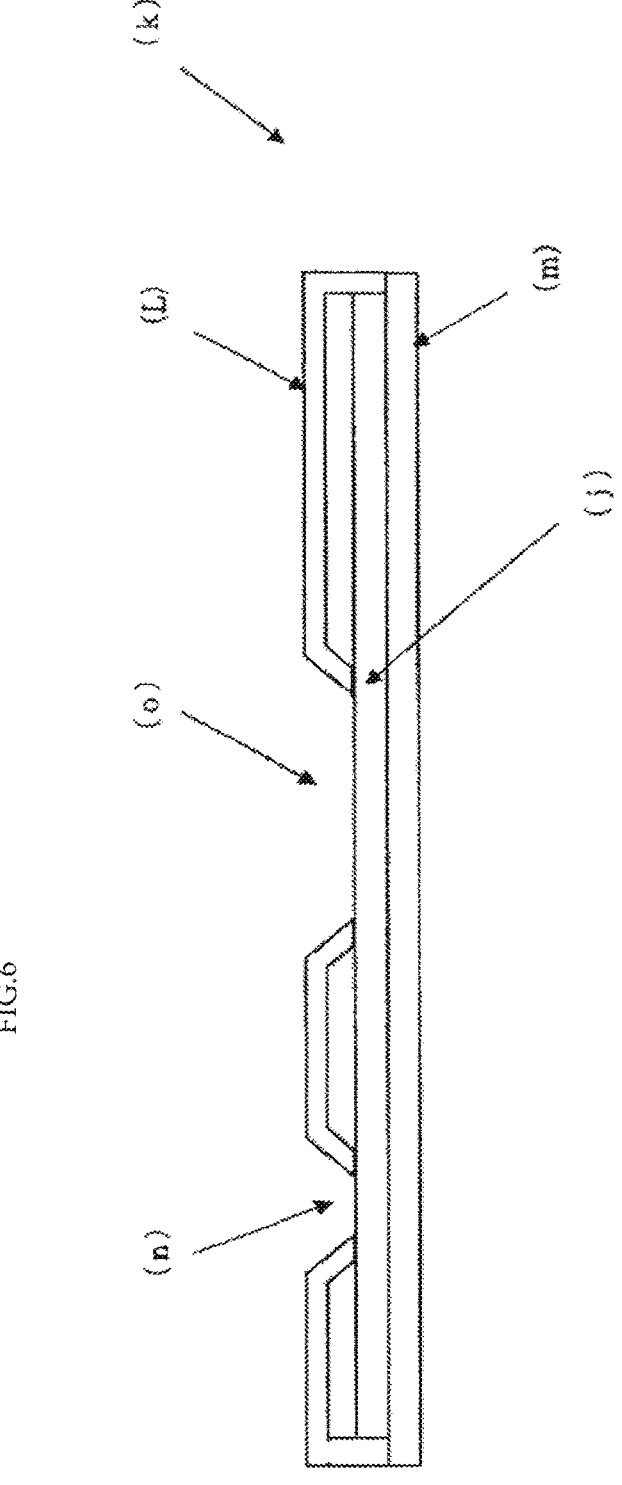
FIG. 6 shows a cut section when the device shown in FIG. 5 is cut along a dotted line.

The test strip for immunochromatography of the present invention can be stored/mounted and used in a suitable container (housing) in consideration of the size of the test strip, the method and position of addition of the specimen, the immobilization position of the specific binding substance on the specific binding substance-immobilized membrane, a signal detection method, etc., and the state of being stored/mounted in this way is referred to as a "device". FIGS. 5 and 6 show an example of the device of the present invention in a top view and a cross-sectional view.

(Others)

In this description, the "porous membrane" may be represented as a "solid phase", and physically or chemically supporting the specific binding substance such as an antigen or an antibody with the porous membrane or the supporting state may be represented as "immobilizing", "immobilized", "solid phased", "sensitization", or "adsorption".

(Specimen)

In the detection method of the present invention, the "specimen" containing the analyte refers to a biological sample such as blood, urine, sputum, saliva, nasal discharge, nasal cavity swab, throat swab, other body fluids, and feces. The biological sample may directly be used as a specimen, and a sample appropriately diluted with a diluent or extracted and/or filtered is also included in the specimen of the present invention. Examples of blood specimens include whole blood, erythrocytes, plasma, serum, etc.

The blood specimen also includes a specimen collected by a blood collection tube to which an anticoagulant such as EDTA or heparin is added at the time of blood collection.

(Analyte)

The analyte of the present invention is a substance present in a biological specimen such as blood (whole blood), erythrocytes, serum, plasma, urine, saliva, or sputum and examples thereof include: inflammation-related labels such as CRP (C-reactive protein), IgA, IgG, and IgM; coagulation or fibrinolysis labels such as fibrin degradation products (e.g., D-dimer), soluble fibrin, TAT (thrombin-antithrombin complex), and PIC (plasmin-plasmin inhibitor complex); circulation-related labels such as oxidized LDL, BNP (brain natriuretic peptide), H-FABP (cardiac fatty acid-binding protein), cardiac troponin I (cTnI); metabolism-related labels such as adiponectin; tumor labels such as CEA (carcinoembryonic antigen), AFP (α-fetoprotein), CA19-9, CA125, and PSA (prostate-specific antigen); infectious disease-related labels such as HBV (hepatitis B virus), HCV (hepatitis C virus), *Chlamydia trachomatis*, and gonococcus; allergen-specific IgE (immunoglobulin E), hormones, and drugs. Among these, D-dimer, CRP, BNP, H-FABP, cTnI, etc. associated with a high desire to use whole blood as a specimen are more preferable.
(Specific Binding Substance)

In the present invention, examples of the specific binding substance for an analyte supported by insoluble carrier particles such as colloidal gold and the porous membrane include proteins, peptides, amino acids, lipids, sugars, DNA, RNA, receptors, and haptens, and although not particularly limited by the magnitude of molecular weight or the origin such as natural or synthetic, examples thereof include antibodies or antigens that may be used in immunological measurement methods utilizing an immune response.
(Antibody Used in the Present Invention)

The antibody to the analyte used in the present invention is not limited by a method of preparation as long as the antibody specifically reacts with the analyte, and may be a polyclonal antibody or a monoclonal antibody. More preferably, the antibody is a monoclonal antibody. In general, hybridomas producing the antibody can be prepared by cell fusion between the spleen cells of an animal immunized by using the analyte as an immunogen and the myeloma cells of the same species according to the method of Kohler and Milstein (see Nature, Vol. 256, p. 495 (1975)).

The antibody of the present invention can be a whole antibody molecule as well as a functional fragment of an antibody having an antigen-antibody reaction activity. The antibody may be an antibody obtained through an immunization step of general animals (mouse, goat, sheep, etc.), as well as an antibody having an amino acid sequence changed to that of an animal species different from the animal immunized with the immunogen (analyte) by a gene recombination technique, etc. (such as a chimera specific binding substance, a humanized antibody, or a fully humanized antibody). Examples of the functional fragment of the antibody include F(ab')$_2$ or Fab', which is a fragment having an antigen-antibody reaction activity, and a single-chain antibody (scFv). These functional fragments can be produced by treating the antibody obtained as described above with a proteolytic enzyme (e.g., pepsin or papain).

In a relationship between an antibody for immobilization on a label (first antibody) and an antibody for immobilization on a porous membrane (second antibody) when the antibodies used in the measurement method for detecting an analyte through so-called sandwich formation are monoclonal antibodies, the epitope of the second antibody used is different from that of the first antibody when the epitope of the first antibody is monovalent, and the epitope of the second antibody used may be the same as or different from that of the first antibody when the epitope of the first antibody is polyvalent.
(Kit)

A detection kit utilizing the immunochromatographic test strip of the present invention may be a kit that includes an immunochromatographic test strip including at least a porous membrane and having a sample application region, a development region, and a detection region on which an antibody is immobilized, and the immunochromatographic test strip is characterized in that an opaque base material is arranged on the back surface of the porous membrane.

The detection kit may include another reagent required for detection (e.g., a detection reagent containing a conjugate), a specimen diluent, a test tube, a cotton swab for feces collection, an instruction manual, a housing for storing the test strip, etc.

Specific examples of the present invention will hereinafter be described; however, these are for illustrative purposes only, and the present invention is not limited thereto.

EXAMPLES

Test Example 1

Confirmation Test for Effect of Avoiding Bleaching Phenomenon

An effect of avoiding the bleaching phenomenon in the case of using the antibody-immobilized membrane lined with a white base material of the present invention was compared with the case of lining with the conventional transparent base material.
1. Fabrication of Immunochromatographic Detection Device of the Present Invention
1) Preparation of Colloidal Gold-Labeled Anti-cTnI Monoclonal Antibody (Anti-cTnI Antibody Conjugate)
(i) Preparation of Colloidal Gold Solution (60 nm)

To 5000 mL of purified water heated to 93° C., 10 mL of a 7% (w/v) triammonium citrate aqueous solution was added and mixed by stirring. Subsequently, 10 mL of a 5% (w/v) tetrachloroauric(III) acid aqueous solution was added and reacted for 10 minutes with stirring, and the reaction solution was then boiled. Subsequently, the solution was cooled in ice water to prepare a solution of colloidal gold having an average particle diameter of 60 nm.

This solution of colloidal gold having an average particle diameter of 60 nm was adjusted with purified water to an absorbance of 1 OD/mL at the maximum absorption wavelength of colloidal gold.
(ii) Preparation of Anti-cTnI Antibody Conjugate To 200 mL of the 1 OD/mL 60 nm colloidal gold solution (pH 8.0), 10 mL of an anti-cTnI monoclonal antibody diluted to 69.3 μg/mL with a 2 mM Tris-hydrochloric acid buffer solution (pH 7.0) was added and stirred for 10 minutes at room temperature. To the mixture liquid of the colloidal gold and the antibody, 10 mL of purified water containing 0.5% (w/v) of Neo Protein Saver (Toyobo, No. NPS-301) was added and stirred for 5 minutes at room temperature. Subsequently, the mixture was centrifuged at 11900×g for 45 minutes at 10° C. After removing a supernatant, 10 mL of a 0.2% (w/v) Neo Protein Saver aqueous solution was added to an obtained sediment to suspend a conjugate to obtain an anti-cTnI antibody conjugate.
(iii) Preparation of Colloidal Gold Solution (40 nm)

To 5000 mL of purified water heated to 73° C., 10 mL of a 5% (w/v) triammonium citrate aqueous solution was added and mixed by stirring. Subsequently, 10 mL of a 5% (w/v) tetrachloroauric(III) acid aqueous solution was added and reacted for 10 minutes with stirring, and the reaction solution was then boiled. Subsequently, the solution was cooled in ice water to prepare a solution of colloidal gold having an average particle diameter of 40 nm.

This solution of colloidal gold having an average particle diameter of 40 nm was adjusted with purified water to an absorbance of 1 OD/mL at the maximum absorption wavelength of colloidal gold.
(iv) Preparation of Colloidal Gold-Labeled KLH (KLH conjugate) for Control Line To 200 mL of the 1 OD/mL 40 nm colloidal gold solution (pH 6.1), 2.67 mL of KLH (manufactured by Sigma) dissolved in a 2 mM phosphate buffer solution (pH 6.1) to 375 μg/mL was added and stirred for 10 minutes at room temperature. To the mixture liquid of the colloidal gold and KLH, 20 mL of a 10% bovine serum albumin (BSA)

aqueous solution was added and stirred for 5 minutes at room temperature. Subsequently, the mixture was centrifuged at 10° C. for 45 minutes, and after removing a supernatant, 10.7 mL of Conjugate Dilution Buffer (Scripps) was added to an obtained sediment to suspend a conjugate to obtain a KLH conjugate.

2) Fabrication of Conjugate Pad

A conjugate solution was prepared by mixing the anti-cTnI antibody conjugate (3 OD), the KLH conjugate (0.75 OD), 0.5% LipidureBL-1301, 0.25 mg/ml Heteroblock, 2.4% lactose, 2.0% NPS, 20 mM MOPS (pH 7.2), and a 1/6 amount of Conjugate Dilution Buffer based on the total amount, and a glass fiber pad (Merck Millipore) having a fixed volume is imbued with a 1.2-fold amount of the solution relative to the volume of the pad. The pad was dried by heating in a dry oven at 70° C. for 45 minutes to obtain a conjugate pad.

3) Fabrication of Anti-cTnI Monoclonal Antibody-Immobilized Membrane (Antibody-Immobilized Membrane)

For a test line, the anti-cTnI monoclonal antibody was diluted to 3 mg/mL with 10 mM PB (containing 0.09% $NaN_3$) (pH 8.0) containing 2.5% sucrose.

For a control line, a rabbit anti-KLH polyclonal antibody (manufactured by Bethyl) was diluted to 1 mg/mL with 10 mM PB (containing 0.09% $NaN_3$) (pH 7.2) containing 2.5% sucrose.

At a position on the short side of a nitrocellulose membrane lined with a transparent or white base material shown in Table 1, the anti-cTnI monoclonal antibody was set to 1 μL/cm and applied in a line shape by using the immuno-chromatographic dispenser "XYZ3050" (BIO DOT) to form the test line. The anti-KLH polyclonal antibody was similarly applied at intervals of about 4 mm from the position of the test line to form the control line. The membrane was dried at 70° C. for 45 minutes in a dry oven to obtain an antibody-immobilized membrane.

4) Fabrication of Sample Pad

A sample pad pretreatment solution was obtained by adjusting 20 mM MOPS (pH 7.2) containing 0.5% lactose and 2% polybrene.

A glass fiber pad (Lydall) was cut to an appropriate size, infused with a 1.5-fold amount of the sample pad pretreatment solution relative to the volume of the pad, and dried in a dry oven at 70° C. for 45 minutes, and was used as a sample pad.

5) Fabrication of Immunochromatographic Test Strip

The antibody-immobilized porous membrane (b-1) lined with each of the base materials (b-2) was affixed to the backing sheet (a), application parts are arranged such that the anti-cTnI antibody (c) on the upstream side of development is followed by the anti-KLH antibody (d), and the blood cell separation membrane (3rd pad) (e) was further mounted on the membrane. Subsequently, the conjugate pad (f) fabricated in 2) was arranged and mounted; the sample pad (g) fabricated in 4) was arranged and mounted to overlap the conjugate pad; and the absorption pad (h) was arranged and mounted at an end on the opposite side.

Finally, the surfaces of the absorption pad and the antibody-immobilized membrane were covered with a top film (i) such that a portion of the antibody-immobilized membrane was exposed. By cutting into a structure having the constituent elements overlapped with each other in this way, an immunochromatographic test strip was fabricated. FIG. 4 shows a schematic configuration diagram of the immunochromatographic test strip.

The test strip may be stored in/mounted on a dedicated plastic housing in a form of an immunochromatographic test detection device. FIGS. 5 and 6 show a schematic top view and a schematic cross-sectional view of an immunochromatographic detection device (k). Reference numeral (n) denotes a sample addition window part, (o) denotes a detection window part, (L) and (m) denote housings, and (j) denotes the immunochromatographic test strip.

2. Detection or Measurement by Immunochromatography

To the sample pad window part of the immunochromatographic test detection device prepared as described above, 120 μL of a plasma specimen solution containing cardiac troponin I (cTnI) having any concentration in the range of 0 to 10 ng/mL was added, and visual observation was performed 15 minutes later near the test line to evaluate the presence or absence of bleaching. The results are shown in Table 1.

<Bleaching Evaluation Criteria>

By visually evaluating 12 or 20 samples, bleaching was considered as being "present" when bleaching was recognized in even one sample, and bleaching was considered as being "absent" when no sample had bleaching.

TABLE 1

| Base material | Manufacturer | Name | Bleaching |
|---|---|---|---|
| Transparent | Merck Millipore | Hi-Flow PlusHF180 | Present |
| White | Sartorius | Unisart ® CN150 | Absent |
| Transparent | Sartorius | Unisart ® CN140 | Present |
| Transparent | Sartorius | Unisart ® CN95 | Present |
| Transparent | GE Healthcare | ImmunoporeSP | Present |
| Transparent | GE Healthcare | FF80HP | Present |
| Transparent | GE Healthcare | FF120HP | Present |
| Transparent | GE Healthcare | FF170HP | Present |

3. Results

In each case when the nitrocellulose membrane lined with a transparent base material was used as the antibody-immobilized membrane, the bleaching phenomenon was observed shortly before the test line; however, when the nitrocellulose membrane lined with a white base material of the present invention was used as the antibody-immobilized membrane, the bleaching phenomenon was not observed. Therefore, the visibility is improved in visual evaluation of immunochromatographic tests, so that more accurate evaluation can be made.

Although bleaching was determined/evaluated by visual observation in this example, if the optical measurement was performed by using an apparatus, disturbance of waveform can be avoided, and the baseline can correctly be set.

Test Example 2

Confirmation Test for CV Reduction Effect

Variations in measurement values in the case of optical measurement using the antibody-immobilized membrane lined with a white base material of the present invention were compared with the case of lining with conventional transparent base materials.

1. Manufacturing of Immunochromatographic Devices

Immunochromatographic test strips were manufactured as in Test Example 1 except that two types of membranes (HF180, CN140) lined with a transparent base material and a porous membrane (CN150) lined with a white base material of the present invention were used.

2. Detection or Measurement by Immunochromatography

To the sample pad window of the immunochromatographic test device prepared above, 120 μL of a plasma specimen solution containing 40 or 60 pg/mL of cardiac troponin I (cTnI) was added, and coloration amounts (absorbance) of the test line were measured 15 minutes later by using an immunochromatographic reader Rapid Pia (Sekisui Medical Co., Ltd.) to calculate respective CV values (variations). CV refers to coefficient of variation and can be calculated by dividing a standard deviation by a mean value. The results are shown in FIG. 1.

3. Results

When the porous membrane lined with a white base material of the present invention was used as the antibody-immobilized membrane, the CV value decreased as compared to when the membrane lined with the transparent base material was used as the antibody-immobilized membrane, and the reproducibility of measurement was improved.

Test Example 3

Confirmation Test for CV Reduction Effect (Low Concentration Side)

A test was conducted to check whether the variation reduction effect of Test Example 2 appears even when the analyte has a low concentration.

1. Manufacturing of Immunochromatographic Devices

Immunochromatographic test strips were manufactured as in Test Example 1 except that a membrane (CN150) lined with a transparent base material and two lots of porous membranes (CN150) lined with white base materials of the present invention were used.

2. Detection or Measurement by Immunochromatography

Figure 2:
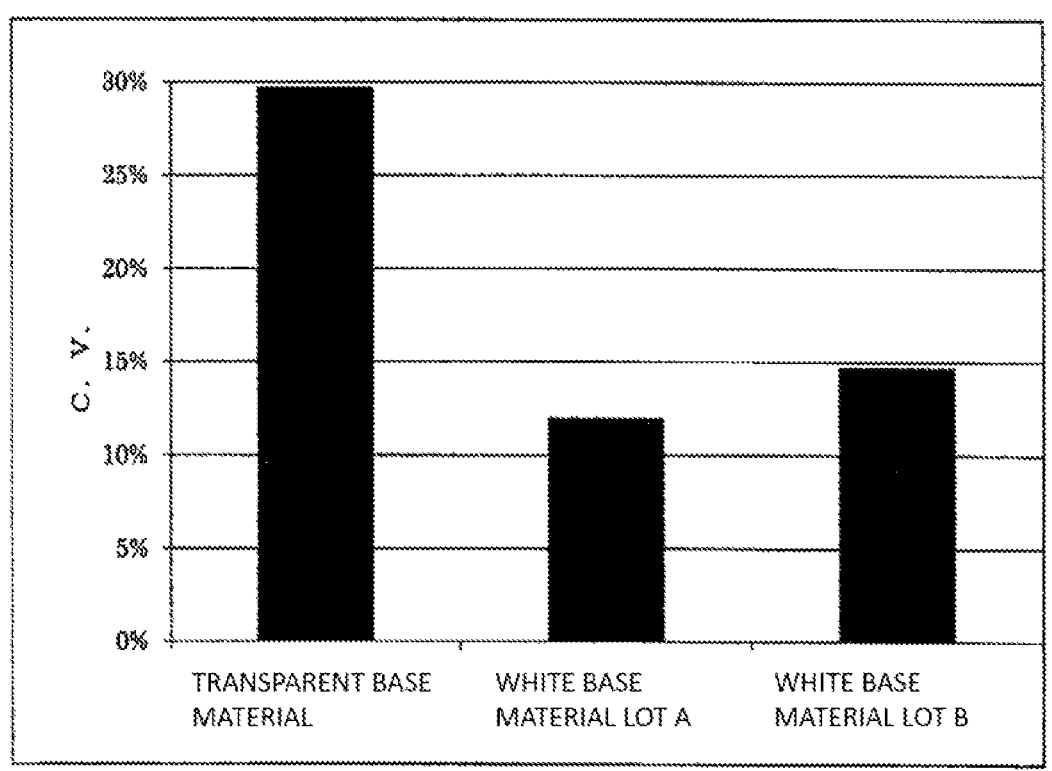
FIG. 2 is a graph showing variations in measurement values when immunochromatographic measurement is performed with an immunochromatographic test strip using a porous membrane in which a lining is made of a transparent base material (Comparative Example) or a white base material (present invention). (Test Example 3, an analyte is on the low concentration side)

Measurement was performed as in Test Example 2 except that a plasma specimen solution containing 15 pg/mL cardiac troponin I (cTnI) was used, and respective CV values (variations) were calculated. The results are shown in FIG. 2.

3. Results

When the porous membranes lined with white base materials of the present invention were used as the antibody-immobilized membranes, the CV value decreased even when the concentration of the analyte is low as compared to when the membrane lined with the transparent base material was used as the antibody-immobilized membrane, and the reproducibility of measurement was improved. Similar results were obtained even when two different lots were used.

Test Example 4

Confirmation Test for CV Reduction Effect (High Concentration Side)

A test was conducted to check whether the variation reduction effect of Test Example 2 appears even when the analyte has a high concentration.

1. Manufacturing of Immunochromatographic Devices

Immunochromatographic test strips were manufactured as in Test Example 1 except that a membrane (CN150) lined with a transparent base material and a porous membrane (CN150) lined with a white base material of the present invention were used.

2. Detection or Measurement by Immunochromatography

Figure 3:
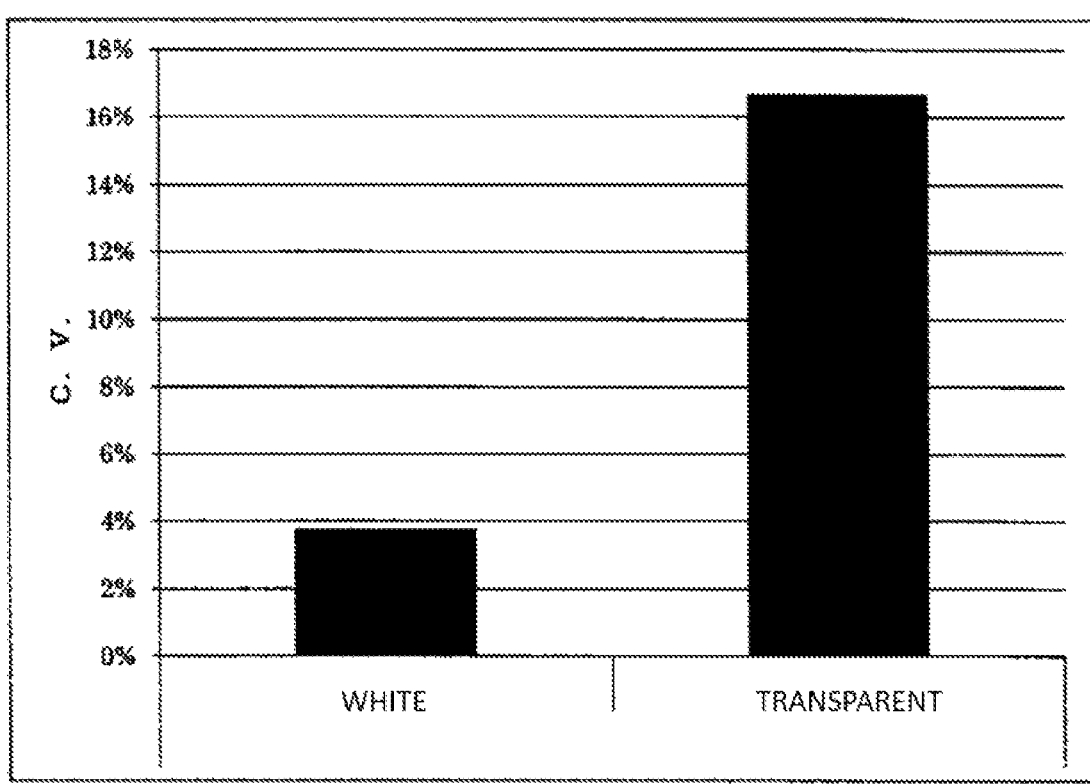
FIG. 3 is a graph showing variations in measurement values when immunochromatographic measurement is performed with an immunochromatographic test strip using a porous membrane in which a lining is made of a transparent base material (Comparative Example) and a white base material (present invention). (Test Example 4, an analyte is on the high concentration side)

Measurement was performed in the same manner as in Test Example 2 except that a plasma specimen solution containing 400 pg/mL cardiac troponin I (cTnI) was used, and respective CV values (variations) were calculated. The results are shown in FIG. 3.

3. Results

When the porous membrane lined with a white base material of the present invention was used as the antibody-immobilized membrane, the CV value significantly decreased even when the concentration of the analyte is low as compared to when the membrane lined with the transparent base material was used as the antibody-immobilized membrane, and the reproducibility of measurement was significantly improved.

INDUSTRIAL APPLICABILITY

According to the immunochromatographic test strip of the present invention comprising at least a porous membrane and having a sample application region, a development region, and a detection region in which a specific binding substance is immobilized, wherein the detection region is immobilized on the front surface of the porous membrane, and wherein an opaque base material is placed on the back surface of the porous membrane, the bleaching near a test line can be avoided.

Additionally, the immunochromatographic test strip causing fewer variations in measurement values can be produced.

According to the present invention, the avoidance of bleaching of the test strip not only obviously improves visibility in visual determination but also reduces variations in measurement values in optical measurement, so that more accurate measurements can be implemented in any detection methods.

REFERENCE SIGNS LIST (a) backing sheet
(b) antibody-immobilized membrane
(b-1) porous membrane
(b-2) backing base material
(c) anti-cTnI antibody (test line)
(d) anti-KLH antibody (control line)
(e) blood cell separation membrane (3rd pad)
(f) conjugate pad
(g) sample pad
(h) absorption pad
(i) top film
(j) immunochromatographic test strip
(k) immunochromatographic detection device
(L) upper housing
(m) lower housing
(n) sample addition window region
(o) detection window region

The invention claimed is:

1. An immunochromatographic test strip comprising at least a sample pad serving as a sample application region, a conjugate pad or a conjugate part in a portion of the sample pad, a porous membrane, a top film and an opaque base material, the immunochromatographic test strip including, a development region, and a detection region, wherein the detection region is immobilized on a front surface of the porous membrane, but a portion of the porous membrane is exposed, wherein the top film is covering an uppermost surface of the immunochromatographic test strip so as to cover the detection region immobilized on the front surface of the porous membrane, and wherein the opaque base material is placed only on a back surface of the porous membrane, wherein, a backing sheet is placed under the sample pad, the conjugate pad or the conjugate part, and the opaque base material, and the thickness of the opaque base material is 80 μm or more and 120 μm or less.

2. The immunochromatographic test strip according to claim 1, wherein the opaque base material is a white base material.

3. The immunochromatographic test strip according to claim 1, wherein the conjugate pad or the conjugate part contains a specific binding substance labeled with colloidal gold, colloidal platinum or colored latex.

4. The immunochromatographic test strip according to claim 3, wherein the specific binding substance is an antibody.

5. The immunochromatographic test strip according to claim 1, wherein the immunochromatographic test strip is a test strip for detection by optical means.

6. An immunochromatographic detection kit comprising: the immunochromatographic test strip according to claim 1.

7. An immunochromatographic detection method which comprises:

providing an immunochromatographic test strip comprising a sample pad serving as a sample application region, a conjugate pad or a conjugate part in a portion of the sample pad, a porous membrane, a top film, and an opaque base material, the porous membrane including at least a detection region with the opaque base material placed only on a back surface of the porous membrane, wherein the top film is covering an uppermost surface of the immunochromatographic test strip so as to cover the detection region immobilized on the front surface of the porous membrane, but a portion of the porous membrane is exposed, and wherein a backing sheet is placed under the sample pad, the conjugate pad or the conjugate part, and the opaque base material, and the thickness of the opaque base material is 80 μm or more and 120 μm or less;

applying a sample to the immunochromatographic test strip; and detecting an optical parameter derived from a labeling substance by an apparatus.

8. The immunochromatographic detection method according to claim 7, wherein the opaque base material is a white base material.

9. The immunochromatographic detection method according to claim 7, wherein the conjugate pad or the conjugate part contains a specific binding substance labeled with colloidal gold or colored latex.

10. The immunochromatographic detection method according to claim 9, wherein the specific binding substance is an antibody.

11. The immunochromatographic detection method according to claim 7, further comprising a step of determining a coloration derived from a labeling substance by visual observation.

12. A method for reducing variation in measurement values in an immunochromatographic detection method which comprises:

providing an immunochromatographic test strip comprising at least a sample pad serving as a sample application region, a conjugate pad or a conjugate part in a portion of the sample pad, a porous membrane, a top film, and an opaque base material, wherein the immunochromatographic test strip includes a development region and a detection region, wherein the detection region is immobilized on a front surface of the porous membrane, wherein the top film is covering an uppermost surface of the immunochromatographic test strip so as to cover the detection region immobilized on the front surface of the porous membrane, but a portion of the porous membrane is exposed, and wherein the opaque base material is placed only on a back surface of the porous membrane, wherein a backing sheet is placed under the sample pad, the conjugate pad or the conjugate part, and the opaque base material, and the thickness of the opaque base material is 80 μm or more and 120 μm or less;

applying a sample to the immunochromatographic test strip; and detecting an optical parameter derived from a labeling substance by an apparatus.

13. The method for reducing the variation according to claim 12, wherein the opaque base material is a white base material.

14. A method for reducing bleaching of a test strip in an immunochromatographic detection method which comprises:

providing immunochromatographic test strip comprising at least a sample pad serving as a sample application region, a conjugate pad or a conjugate part in a portion of the sample pad, a porous membrane, a top film, and an opaque base material, wherein the immunochromatographic test strip includes a development region, and a detection region, wherein the detection region is immobilized on a front surface of the porous membrane, wherein the top film is covering an uppermost surface of the immunochromatographic test strip so as to cover the detection region immobilized on the front surface of the porous membrane, but a portion of the porous membrane is exposed, and wherein the opaque base material is placed only on a back surface of the porous membrane, wherein a backing sheet is placed under the sample pad, the conjugate pad or the conjugate part, and the opaque base material, and the thickness of the opaque base material is 80 μm or more and 120 μm or less;

applying a sample to the immunochromatographic test strip; and detecting an optical parameter derived from a labeling substance by an apparatus.

15. The method for reducing bleaching of a test strip according to claim 14, wherein the opaque base material is a white base material.

16. The immunochromatographic test strip according to claim 1, wherein the backing sheet is a white backing sheet.

17. The immunochromatographic test strip according to claim 2, wherein the backing sheet is a white backing sheet.

18. The immunochromatographic test strip according to claim 1, wherein the immunochromatographic test strip further comprises a blood cell separation membrane or 3rd pad and an absorption pad, and wherein the backing sheet is placed under the sample pad, the conjugate pad or the conjugate part, the blood cell separation membrane or 3rd pad, the opaque base material and the absorption pad.

19. The immunochromatographic detection method according to claim 7, wherein the immunochromatographic test strip further comprises a blood cell separation membrane or 3rd pad and an absorption pad, and wherein the backing sheet is placed under the sample pad, the conjugate pad or the conjugate part, the blood cell separation membrane or 3rd pad, the opaque base material and the absorption pad.

20. The method for reducing the variation according to claim 12, wherein the immunochromatographic test strip further comprises a blood cell separation membrane or 3rd pad and an absorption pad, and wherein the backing sheet is placed under the sample pad, the conjugate pad or the conjugate part, the blood cell separation membrane or 3rd pad, the opaque base material and the absorption pad.

21. The method for reducing bleaching of a test strip according to claim 14, wherein the immunochromatographic test strip further comprises a blood cell separation membrane or 3rd pad and an absorption pad, and wherein the backing sheet is placed under the sample pad, the conjugate pad or the conjugate part, the blood cell separation membrane or 3rd pad, the opaque base material and the absorption pad.

22. The immunochromatographic test strip according to claim 1, wherein the conjugate pad or the conjugate part contains a specific binding substance labeled with colloidal gold or colored latex.

23. The immunochromatographic test strip according to claim 1, wherein the top film is made of polyester.

24. The immunochromatographic test strip according to claim 1, wherein the conjugate pad or the conjugate part contains a specific binding substance labeled with colloidal gold, and the top film is made of polyester.

25. The immunochromatographic test strip according to claim 1, wherein the conjugate pad or the conjugate part contains a specific binding substance labeled with colloidal gold, the backing sheet is a white backing sheet, the top film is made of polyester, and the opaque base material is a white base material.

\*   \*   \*   \*   \*